United States Patent
Hegel et al.

(10) Patent No.: US 10,809,258 B2
(45) Date of Patent: Oct. 20, 2020

(54) METHOD FOR THE DETECTION OF THE PROZONE EFFECT OF PHOTOMETRIC ASSAYS

(71) Applicant: Roche Diagnostics Operations, Inc., Indianapolis, IN (US)

(72) Inventors: Ewelina Hegel, Mannheim (DE); Georg Kurz, Penzberg (DE); Eloisa Lopez-Calle, Ludwigshafen (DE); Josef Roedl, Mutterstadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 676 days.

(21) Appl. No.: 15/042,695

(22) Filed: Feb. 12, 2016

(65) Prior Publication Data

US 2016/0161480 A1 Jun. 9, 2016

Related U.S. Application Data

(63) Continuation of application No. PCT/EP2014/067443, filed on Aug. 14, 2014.

(30) Foreign Application Priority Data

Aug. 15, 2013 (EP) .................................. 13180560

(51) Int. Cl.
*G01N 33/48* (2006.01)
*G01N 33/557* (2006.01)
*G01N 33/53* (2006.01)

(52) U.S. Cl.
CPC ....... *G01N 33/557* (2013.01); *G01N 33/5306* (2013.01); *G01N 2333/76* (2013.01)

(58) Field of Classification Search
None
See application file for complete search history.

(56) References Cited

U.S. PATENT DOCUMENTS

| | | | | |
|---|---|---|---|---|
| 6,284,472 B1* | 9/2001 | Wei | ......................... | C07K 16/40 422/400 |
| 6,339,472 B1* | 1/2002 | Hafeman | .................. | G01J 3/08 356/433 |
| 2007/0243559 A1* | 10/2007 | Gunzer | .............. | G01N 33/5306 435/7.1 |
| 2008/0056944 A1* | 3/2008 | Nakamura | ........ | G01N 35/00663 422/67 |
| 2010/0227323 A1* | 9/2010 | Baeumner | ......... | G01N 27/44721 435/6.19 |
| 2011/0157580 A1* | 6/2011 | Nogami | .................. | G01N 1/405 356/36 |
| 2012/0046203 A1* | 2/2012 | Walsh | ................. | A61B 5/15186 506/39 |
| 2013/0132022 A1* | 5/2013 | Tamura | .............. | G01N 15/0211 702/104 |
| 2013/0280696 A1* | 10/2013 | Millenson | ......... | G01N 33/56988 435/5 |

FOREIGN PATENT DOCUMENTS

| | | |
|---|---|---|
| EP | 0898169 B1 | 2/2002 |
| EP | 1643246 A1 | 4/2006 |
| EP | 1845373 A1 | 10/2007 |
| JP | 63-019560 A | 1/1988 |
| JP | H04-204378 A | 7/1992 |
| JP | 05-093725 A | 4/1993 |
| JP | 06-094717 A | 4/1994 |
| JP | 06-213893 A | 10/1994 |
| JP | 10-282099 A | 10/1998 |
| WO | 2009/117510 A2 | 9/2009 |

OTHER PUBLICATIONS

Armbruster, David A. and Pry, Terry, Limit of Blank, Limit of Detection and Limit of Quantitation, The Clinical Biochemist Reviews, 2008, pp. S49-S52, vol. 29, Supplement I.
Molina-Bolívar, J. A. and Galisteo-González F., Latex Immunoagglutination Assays, Journal of Macromolecular Science Part C—Polymer Reviews, 2005, pp. 59-98, vol. 45.
3AKKER, Andries J. et al., (Micro)Albuminuria: Antigen Excess Detection in the Roche Modular Analyzer, Clinical Chemistry, 2005, pp. 1070-1071, vol. 51, No. 6.
International Preliminary Report on Patentability dated Oct. 26, 2015, in Application No. PCT/EP2014/067443, 12 pages.
International Search Report dated Sep. 26, 2014, in Application No. PCT/EP2014/067443, 4 pages.
Jhang, Jeffrey S. et al., Evaluation of Linearity in the Clinical Laboratory, Archives of Pathology & Laboratory Medicine, 2004, pp. 44-48, vol. 128.
Kelly, Alan et al., A Bichromatic Method for Total Bilirubin with a CentrifiChem 400, Clinical Chemistry, 1979, pp. 1482-1484, vol. 25, No. 8.
Klima, H. et al., Development of a System Check (Prozone Check) for Total Bilirubin Test (BILTS) on Roche cobas c 311 and cobas e 501 Systems, Clinical Chemistry, 2009, p. A155, vol. 55, No. 6, Supplement S.

(Continued)

*Primary Examiner* — Anna Skibinsky
(74) *Attorney, Agent, or Firm* — Stinson LLP

(57) ABSTRACT

A method for determination of the amount of a specific analyte in a sample which may show a prozone effect by photometric assays, wherein the specific analyte is quantified from the change in the optical signal of the reaction mixture after the interaction of the analyte with analyte specific assay reagents. The optical signal is measured simultaneously for the specific analyte in the sample to be determined at the wavelength used for the determination of the analyte and at least at an additional specific wavelength used for the detection of the prozone effect over the complete reaction time. The reaction rate ratio R is calculated by using the signals obtained at the wavelength used for the detection of the prozone effect. By comparison of the calculated ratio value R with predetermined limit values it is judged if a prozone effect is present in the sample.

10 Claims, 8 Drawing Sheets

(56) References Cited

OTHER PUBLICATIONS

Papik, Kornel et al., Automated Prozone Effect Detection in Ferritin Homogeneous Immunoassays Using Neural Network Classifiers, Clinical Chemistry and Laboratory Medicine, 1999, pp. 471-476, vol. 37, No. 4.
Roche Diagnostics GmbH, cobas 6000 COBI-CD Compendium, Version 1.0, 2005, pp. 1-F6.

* cited by examiner

Figure 3

$$PC = [v(pmp_3, pmp_4) / v(pmp_1, pmp_2)] \times 100 \text{ with}$$

$$v(pmp_3, pmp_4) = (Apmp_4 - Apmp_3) / (pmp_4 - pmp_3)$$

$$v(pmp_1, pmp_2) = (Apmp_2 - Apmp_1) / (pmp_2 - pmp_1)$$

| | |
|---|---|
| $PC$ | Prozone check value |
| $pmp_n$ | Prozone measure point n (with n = 1, 2, 3, or 4) |
| $v(pmp_n, pmp_m)$ | Rate of change in absorbance between $pmp_n$ and $pmp_m$ |
| $Apmp_n - Apmp_m$ | Absorbance difference between $pmp_n$ and $pmp_m$ |
| $pmp_n - pmp_m$ | Time difference between $pmp_n$ and $pmp_m$ |

Figure 4

To the right of the Prozone Limit field there are nine boxes:

[ lower limit ] [ upper limit ] [ $pmp_1$ ] [ $pmp_2$ ] [ $pmp_3$ ] [ $pmp_4$ ] [ comp. ] [ 0 ] [ 0 ]

- The first two boxes indicate the lower and upper prozone limits
- The next four boxes are for the prozone measure points ( $pmp$ ):
  - 3rd entry: First prozone measure point ($pmp_1$)
  - 4th entry: Second prozone measure point ($pmp_2$)
  - 5th entry: Third prozone measure point ($pmp_3$)
  - 6th entry: Fourth prozone measure point ($pmp_4$)

Appropriate values are: $1 \leq pmp_1 < pmp_2 \leq 57$ and $1 \leq pmp_3 < pmp_4 \leq 57$. If all entries are set to zero, prozone check is not performed.

- The seventh box (Inside/Outside) indicates in which case a data alarm (>Kin) is issued: If the entry is set to Inside, an alarm is issued in case the obtained check value lies *inside* the defined range between the lower and upper prozone limits (first two boxes).
  Vice versa if the entry is set to Outside, an alarm is issued in case the obtained check value lies *outside* the defined range.

- The eighth and ninth boxes define additional conditions for the reaction rate method. These allow you to neglect the prozone check in case the reaction rates get too low.

The entry in the eighth box defines the limit (in Abs $\times 10^4$) for the difference in absorbance between $pmp_1$ and $pmp_2$. If the measured difference between these points falls below the limit, the prozone check is neglected.—In other words:

If $|Apmp_2 - Apmp_1| < F \times 10^{-4}$, reaction rate prozone check is not performed, where $F$ is defined in the eighth box Likewise, the ninth box defines the limit between $pmp_3$ and $pmp_4$. If the measured difference falls below the limit, the prozone check is neglected.—In other words:

If $|Apmp_4 - Apmp_3| < G \times 10^{-4}$, reaction rate prozone check is not performed, where $G$ is defined in the last box of the Prozone Limit line.

| Wavelength | Assay Points, v(start), v(end) | PCV Non-Hook = 923 mg/L | PCV Hook = 1003 mg/L | NPCV Non-Hook % | NPCV Hook % | differentiation | IF |
|---|---|---|---|---|---|---|---|
| 570-800 nm | 11-8, 19-16 | 15.0 | 14.7 | 100 | 98 | 2 | Standard |
| 660-800 nm | 10-8, 20-17 | 17.2 | 16.2 | 100 | 94 | 6 | 2.7 |

| Wavelength | Assay Points, v(start), v(end) | PCV Non-Hook = 1250 µg/L | PCV Hook = 2500 µg/L | NPCV Non-Hook % | NPCV Hook % | differentiation | IF |
|---|---|---|---|---|---|---|---|
| 570-800 nm | 29-25, 47-43 | 10.8 | 8.6 | 100 | 79.273 | 21 | Standard |
| 505-800 nm | 26-24, 43-41 | 6.9 | 4.4 | 100 | 63.445 | 37 | 1.76 |

METHOD FOR THE DETECTION OF THE PROZONE EFFECT OF PHOTOMETRIC ASSAYS

CROSS-REFERENCE TO RELATED APPLICATIONS

This application is a continuation of International Patent Application No. PCT/EP2014/067443, filed 14 Aug. 2014, which claims the benefit of European Patent Application No. 13180560.8, filed 15 Aug. 2013, the disclosures of which are hereby incorporated by reference in their entirety.

TECHNICAL FIELD

The present disclosure relates to the field of medical technology and diagnostics and, in particular, to a method for the determination of the amount of a specific analyte in a sample by photometric, turbidimetric or nephelometric immunoassays combined with a judgment if a prozone effect is present or not, wherein the specific analyte is quantified from the change in the optical signal of the reaction mixture after the interaction of the analyte with analyte specific assay reagents.

BACKGROUND

Homogeneous immunoassays are characterized by a procedure that is free of separation and washing steps. Due to their easy one-step procedure, cost-efficiency and speed, homogeneous immunoassays enjoy a high popularity in clinical laboratories and are routinely used for the clinical diagnosis on highly automated clinical chemistry analyzers.

However, homogeneous immunoassays are limited by the high-dose Hook effect, also called prozone effect or antigen excess effect, a phenomenon where the assay response at high analyte concentrations decrease and results in falsely lower measured values of the analyte. This effect has been reported for many analytes and affects turbidimetric and nephelometric assays as well as other one-step immunoassays, and is caused by excessively high concentrations of analyte, which saturates the binding sites of the antibodies, thus preventing the formation of detectable antibody-analyte-antibody complexes. In this way, the assay response firstly increases with increasing antigen concentration and then after reaching a critical concentration value the assay response decreases yielding a bell shaped curve, the so-called Heidelberger curve. Assay developers and manufacturers usually make every effort to reduce the Hook effect, e.g., by increasing the quantity of the antibodies and by reducing the quantity of sample volumes required for the analysis. In conclusion, the high dose hook effect is a phenomenon that is inherent with one step immunoassay designs; in a two-step assay format, which uses wash steps to eliminate antigen excess, the high dose Hook effect is avoided. Prozone effects may also be observed in other one-step binding assays that use non-antibody based binders.

Most modern automated analyzers used in clinical chemistry have built in methods for recognizing the prozone effect in the measured samples. In case that a sample shows a prozone effect, the sample measurement is flagged by the analyzer. For such flagged measurements, a re-measurement of the sample after a dilution is recommended or even performed automatically by the analyzer, depending on the instrument setting.

There are several methods for judging whether a prozone effect is present in a sample:

The sample dilution method verifies the existence of a prozone effect by testing undiluted samples and samples after dilution. If the result on dilution is higher than for the undiluted sample, then the undiluted sample most likely exhibited the prozone effect. Unfortunately, this approach increases labor and reagent costs.

For the antigen re-addition method, additional analyte is added to the sample after its measurement is completed and the additional change in the signal is interpreted. Although this method is accurate in detecting the prozone effect, the reagent costs are increased due to the antigen addition. In addition, the workflow on the analyzer is increased by the additional pipetting step thus leading to reduced throughput. Furthermore, additional space on the analyzer is occupied by the antigen reagent.

The kinetic method verifies the existence of an antigen excess by analysis of the kinetic data obtained during the sample measurement. In most cases the reaction kinetic depends on the analyte concentration: low concentrated samples may show increasing signals, while high concentrated samples may show a more rapid signal increase at the beginning and much lower at the end of the reaction. The described difference can be used to recognize the presence of the prozone effect.

The kinetic method applied on the Roche cobas c analyzers is also called reaction rate method. Here, the rate of change in absorbance at two different times after final reagent addition is compared (see, Roche cobas c operator manuals; Roche cobas c operator manual training): the ratio of the reaction rate at the end of the reaction and the reaction rate at the beginning of the reaction, expressed as a percentage, is defined as the prozone check value PC. For each assay the specific PC ranges, defined as the range between a lower limit and an upper limit, indicating a prozone effect are stored in the assay settings, and automatically compared with the PC values obtained after the measurement of each sample (see, FIGS. 2, 3 and 4, from Roche "cobas c 311 Analyzer—COBI CD, Compendium of Background Information"). In case that a prozone effect is present, the result obtained for the sample is flagged with >Kin.

Optionally up to two different limits (see, boxes 8th and 9th of the settings in FIG. 4) may be defined on the Roche cobas c analyzers and applied to each measurement which decides how to proceed before analyzing the prozone check value PC for a sample. These limits are reference values for signals that are obtained from a sample at the wavelength used for the determination of the analyte by calculating the signal change in a certain time period. These limits allow neglecting samples with extremely low reaction rates from a prozone check and classifying such samples directly as non-Hook samples. A disadvantage of the kinetic method used in the Roche cobas c analyzers is that the differentiation between Hook and non-Hook samples is not always optimal thus causing difficulties when applying the method to different lots from the same assay by making a wrong flagging, e.g., flagging as "upper measuring range exceeded" instead of "Hook sample" or vice versa.

A further important disadvantage of this method is that it is not applicable for all assays, e.g., the albumin assay, and in such cases the expensive antigen re-addition method described above has to be applied, which increases the workflow on the analyzer by the additional pipetting step thus leading to reduced throughput. Furthermore, additional space on the analyzer is occupied by the antigen reagent. Several prozone detection methods use simple kinetic data analysis formulae. Analyzers applying such methods are usually switched off because of the high rate of false prozone alarms (Clin. Chem. Lab. Med. 1999).

Known methods use either expensive reagents, require additional measurements, or complex signal evaluation procedures. Furthermore, some methods are not always applicable to all assays.

SUMMARY

It is against the above background that the embodiments of the present disclosure provide certain unobvious advantages and advancements over the prior art. In particular, the inventors have recognized a need for improvements in methods for the detection of the prozone effect of photometric assays.

Although the embodiments of the present disclosure are not limited to specific advantages or functionality, it is noted that the present disclosure provides methods for prozone detection that are cost-effective (without the need to consume any reagents), rapid (by a detection method that is performed simultaneous to the sample quantitation step), easy, safe (with no/low numbers of false prozone alarms), and which can implemented in automated lab analyzers.

In accordance with one embodiment of the present disclosure, a method for determination of the amount of a specific analyte in a sample which may show a prozone effect by photometric assays is provided, wherein the specific analyte is quantified from the change in the optical signal of the reaction mixture after the interaction of the analyte with analyte specific assay reagents, comprising the following steps: a) generating a calibration curve at at least one wavelength and reaction time for the specific analyte of a sample to be determined, and depositing the measurement results in a data management system of the instrument platform; b) measuring simultaneously the optical signal for the specific analyte in the sample to be determined at the wavelength used for the determination of the analyte and at least at an additional specific wavelength used for the detection of the prozone effect over the complete reaction time, which is different to the wavelength used for the determination of the analyte; c) calculating the reaction rate ratio R by using the signals obtained at the wavelength used for the detection of the prozone effect (R=[reaction rate at time period 2/reaction rate at time period 1]×100, with reaction rate at time period 2=[signal(time point4)−signal(time point3)]/[time point4−time point3] and reaction rate at time period 1=[signal(time point2)−signal(time point1)]/[time point2−time point1]); d) judging if a prozone effect is present in the sample by comparison of the calculated ratio value R with predetermined limit values; and e) quantifying the amount of the specific analyte by comparison of the optical signal obtained at the wavelength used for the determination of the analyte with the calibration curve.

In accordance with another embodiment of the present disclosure, a method for determination of the amount of a albumin in a sample, which may show a prozone effect by photometric assays is provided, wherein the specific analyte is quantified from the change in the optical signal of the reaction mixture after the interaction of the analyte with analyte specific assay reagents, comprising the following steps: a) generating a calibration curve at at least one wavelength and reaction time for albumin in a sample to be determined and depositing the measurement results in a data management system of the instrument platform; b) measuring simultaneously the optical signal for the specific analyte in the sample to be determined at the wavelength used for the determination of the analyte and at least at an additional specific wavelength used for the detection of the prozone effect over the complete reaction time, which is different to the wavelength used for the determination of the analyte; c) calculating the reaction rate ratio R by using the signals obtained at the wavelength used for the detection of the prozone effect (R=[reaction rate at time period 2/reaction rate at time period 1]×100, with reaction rate at time period 2=[signal(time point4)−signal(time point3)]/[time point4−time point3] and reaction rate at time period 1=[signal(time point2)−signal(time point1)]/[time point2−time point1]); d) judging if a prozone effect is present in the sample by comparison of the calculated ratio value R with predetermined limit values; and e) quantifying the amount of albumin by comparison of the optical signal obtained at the wavelength used for the determination of the analyte with the calibration curve.

In accordance with embodiments of the present disclosure, a method for determination of the amount of a specific analyte in a sample, which may show a prozone effect, by photometric assays is provided, wherein the specific analyte is quantified from the change in the optical signal of the reaction mixture after the interaction of the analyte with analyte specific assay reagents.

In a first step, a calibration curve at at least one wavelength and reaction time is generated for the specific analyte of a sample to be determined and depositing the measurement results in a data management system of the instrument platform.

The optical signal is measured simultaneously for the specific analyte in the sample to be determined at the wavelength used for the determination of the analyte and at least at an additional specific wavelength used for the detection of the prozone effect over the complete reaction time. This additional wavelength is different to the wavelength used for the determination of the analyte.

In the next step, the reaction rate ratio R is calculated by using the signals obtained at the wavelength used for the detection of the prozone effect $R$=[reaction rate at time period 2/reaction rate at time period 1]×100 with reaction rate at time period 2=[signal(time point4)−signal(time point3)]/[time point4−time point3] and reaction rate at time period 1=[signal(time point2)−signal(time point1)]/[time point2−time point1].

By comparison of the calculated ratio value R with predetermined limit values it is judged if a prozone effect is present in the sample.

Finally, the amount of the specific analyte is quantified by comparison of the optical signal obtained at the wavelength used for the determination of the analyte with the calibration curve.

In accordance with yet another embodiment of the present disclosure, optionally further limits may be defined and applied to each measurement which decides how to proceed before, i.e., before calculating and judging the presence of a Hook effect based on the reaction rate ratio R.

These limits are reference values for signals which are measured at the wavelength used for the determination of the analyte, and/or at the wavelength used for the detection of the prozone effect, and/or other wavelengths. An example for such a limit may be defined for a signal change in a certain time period, for neglecting samples with extremely low reaction rates from a prozone check and classifying such samples directly as non-Hook samples. A further example for such a limit may be defined for a signal change in a certain time period, for deciding if a sample with extremely high reaction rate is immediately categorized as Hook sample or if the judgment is performed after the calculation of the reaction rate ratio R.

In accordance with still yet another embodiment of the present disclosure, an instrument platform using commercially available spectrophotometric laboratory tests is provided for determining the amount of the specific analyte in a sample, which may show a prozone effect, by photometric assays, wherein the data management system of the instrument platform is able to process data of reaction times, calibration points, calibration mode, wavelengths, and for performing simultaneously the analyte determination and the prozone effect detection from one sample measurement.

In accordance with yet still another embodiment of the present disclosure, a method for determination of the amount of a albumin in a sample is provided, which may show a prozone effect, by photometric assays, wherein the specific analyte is quantified from the change in the optical signal of the reaction mixture after the interaction of the analyte with analyte specific assay reagents according the present disclosure.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

BRIEF DESCRIPTION OF THE DRAWINGS

Figure 1:
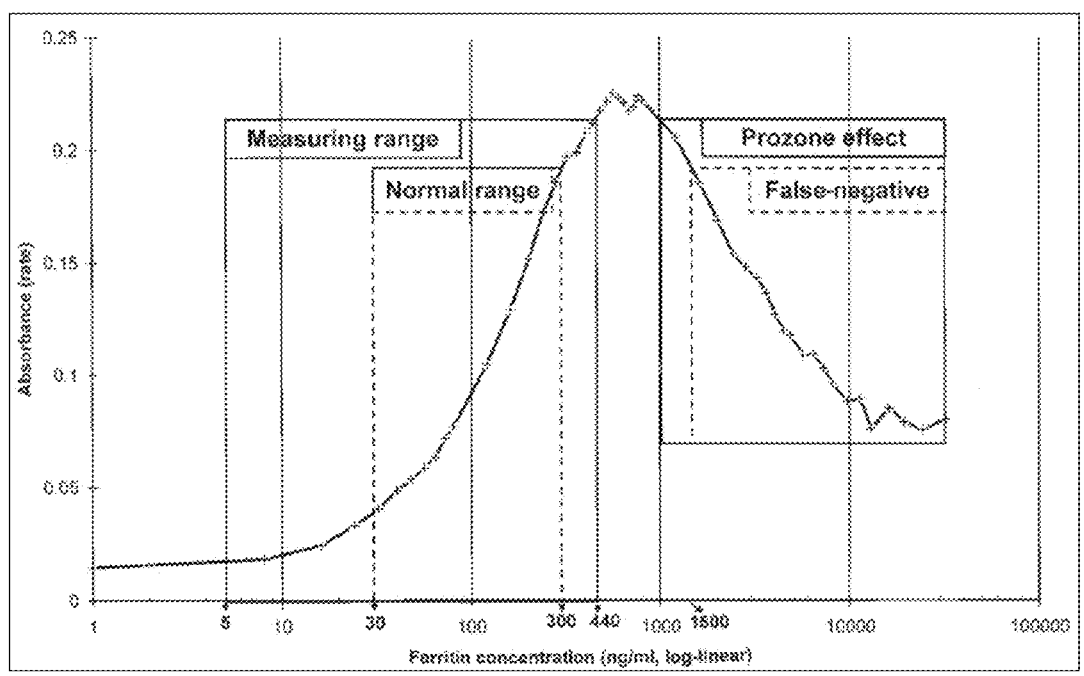
Figure 2:
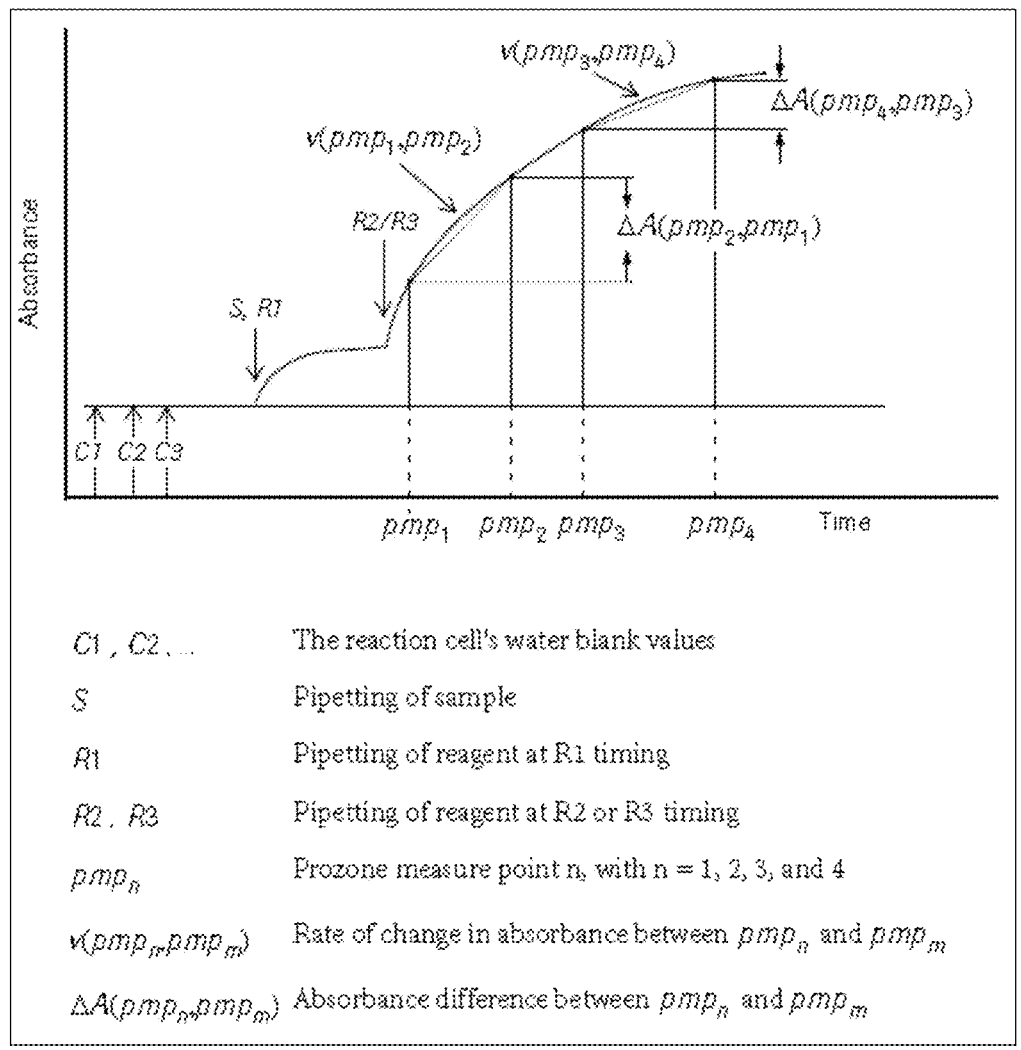
Figures 5A, 5B:
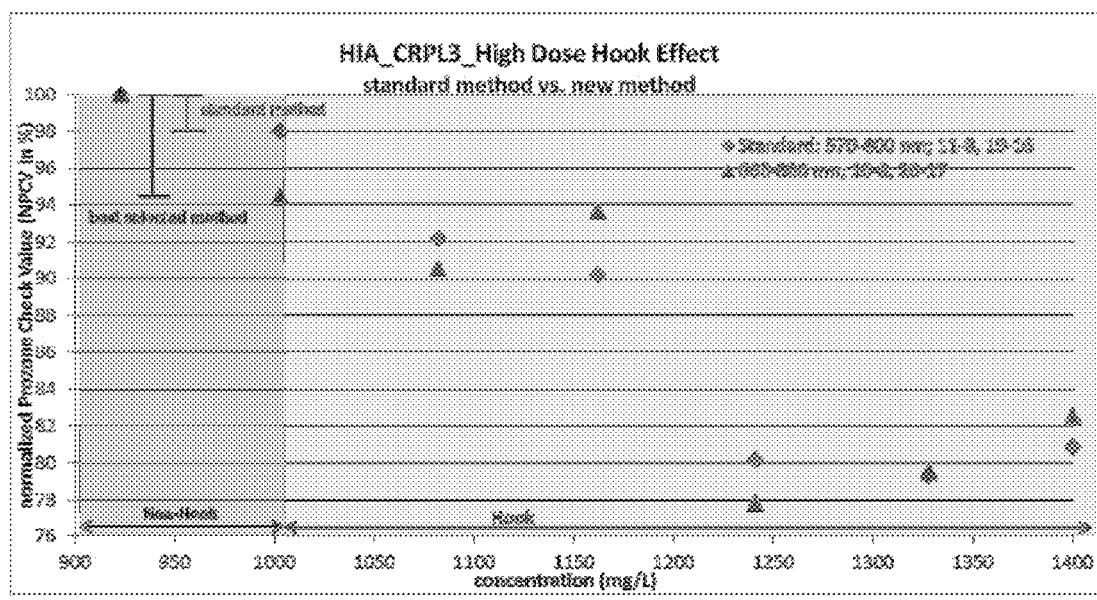
Figures 6A, 6B:
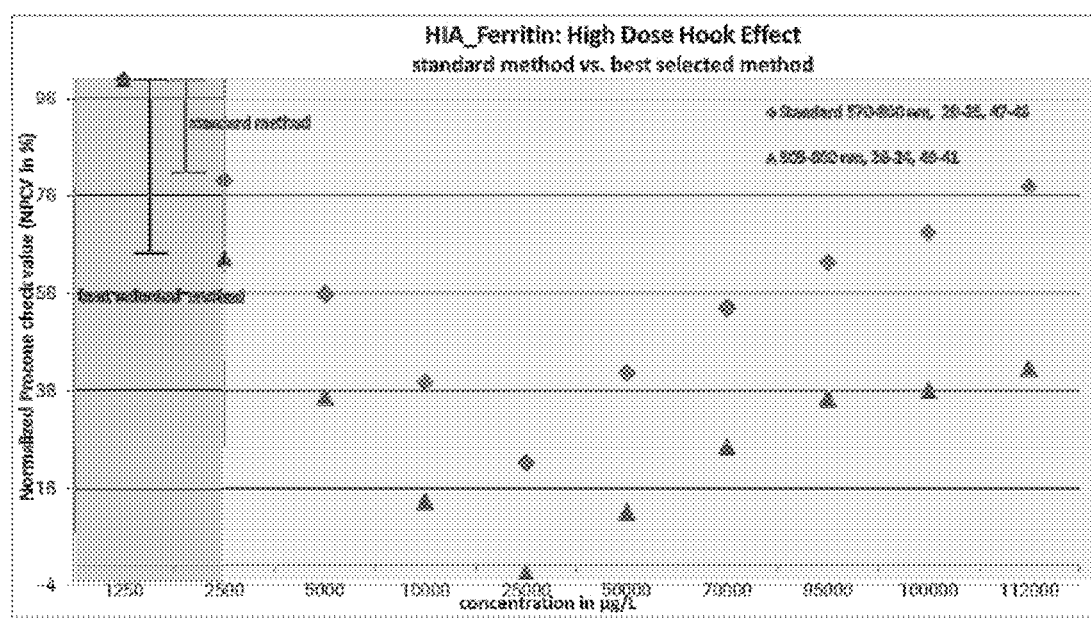
Figure 7A:
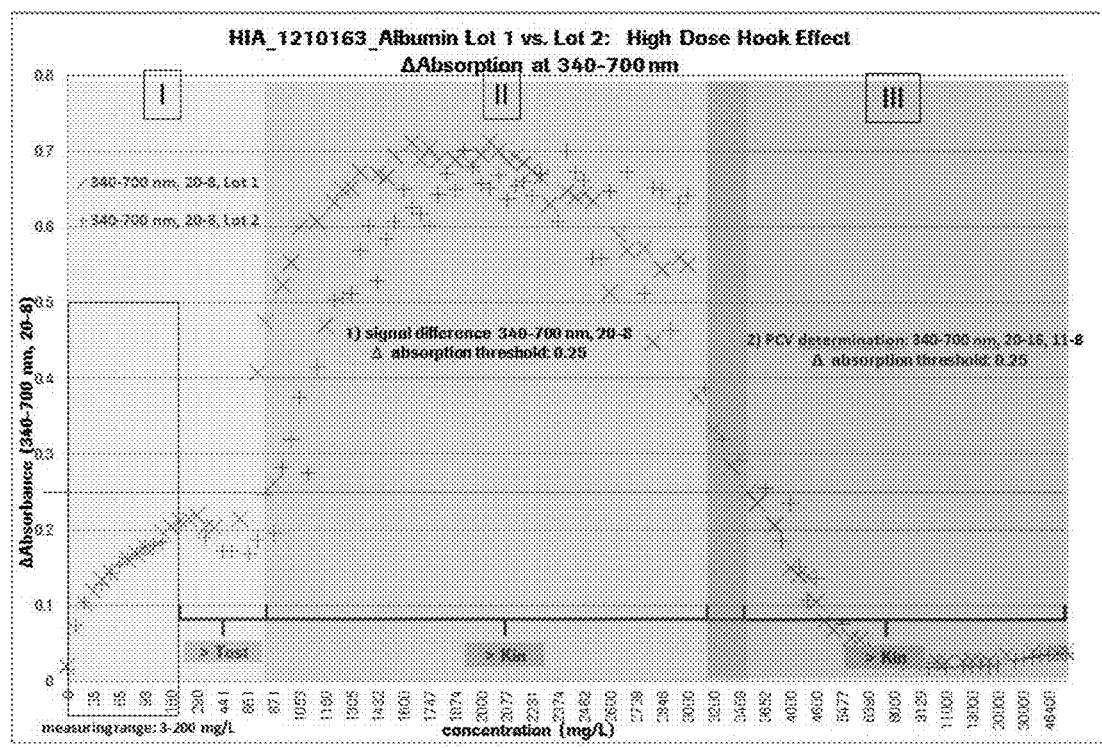
Figure 7B:
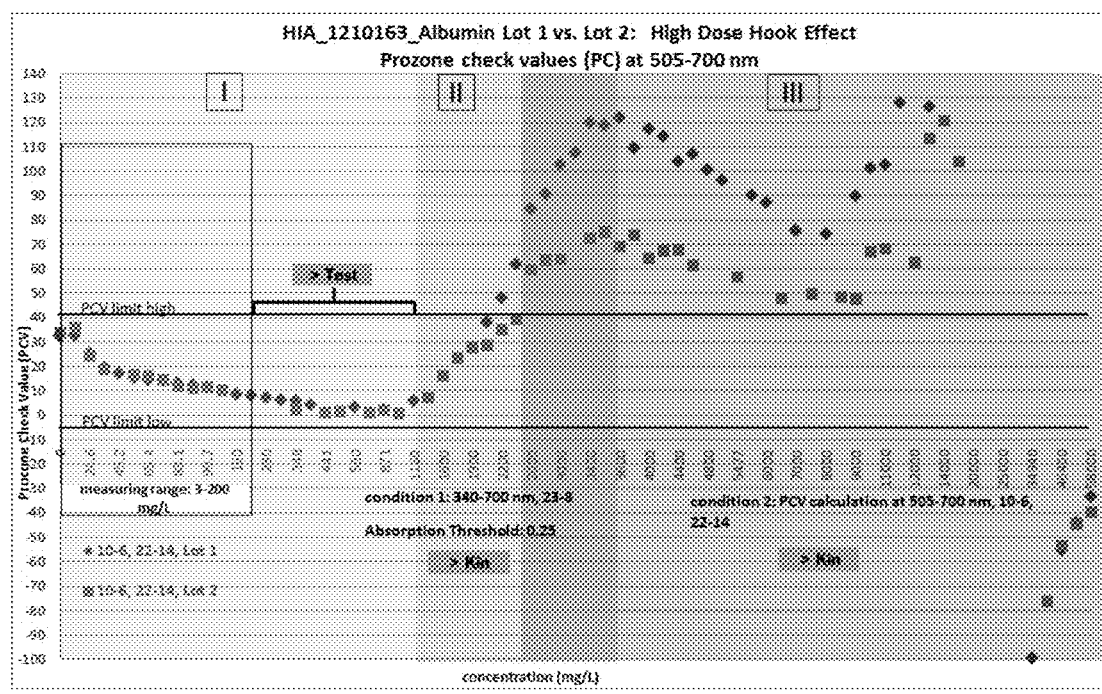

FIG. 1 shows the Heidelberger curve and important ranges of the ferritin homogeneous immunoassay (figure from literature Clin. Chem. Lab. Med 1999, 37, 471-476);

FIG. 2 shows the prozone check on a Roche cobas c analyzer with reaction rate method;

FIG. 3 shows the prozone check value calculation on a Roche cobas c analyzer;

FIG. 4 shows the settings for prozone check with reaction rate method on a Roche cobas c 311 analyzer;

FIGS. 5A and 5B show the differentiation between Hook- and non-Hook samples of the CRP L3 test. FIG. 5A shows a scheme with normalized PC values (NPCV) of standard method and new method. FIG. 5B shows an overview with results obtained with the standard method and the new method as well as the improvement factors IF;

FIGS. 6A and 6B show the differentiation between Hook- and non-Hook samples of the Ferritin assay. FIG. 6A shows a scheme with normalized PC values (NPCV) of standard method and new method. FIG. 6B shows an overview with results obtained with the standard method and the new method as well as the improvement factors IF; and FIGS. 7A and 7B show the differentiation between Hook- and non-Hook samples. FIG. 7A shows a scheme with absorbance readings taken at measurement wavelengths 340 nm-700 nm. The signal difference between measure point 8 and measure point 20 is calculated. The signal difference limit is set to 0.25. All samples showing signal differences >0.25, are Hook samples. For all samples showing signal difference ≤0.25, prozone check is performed. FIG. 7B shows a scheme wherein prozone check values are calculated by applying the reaction rate method (see settings in 3.3.2.1). Signals are generated at measure wavelengths 505 nm-700 nm and used for prozone check value calculation. Samples with PCs outside of the defined limits are Hook samples.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The present disclosure provides an improved method for detecting a prozone phenomenon by analysis of the kinetic data obtained during the sample measurement.

Definitions:

The term "spectrophotometric assay", also called "photometric assay", is well known in the art. Photometric assays encompass turbidimetric and nephelometric immunoassays. In turbidimetric and nephelometric immunoassays the specific analyte is quantified from the change in the turbidity of the reaction mixture based on the agglutination of the specific analyte and an analyte specific binding partner.

The term "turbidimetry and nephelometry" are methods known in the art for determining the amount of cloudiness, or turbidity, in a solution based upon measurement of the effect of this turbidity upon the transmission and scattering of light. Turbidity in a liquid is caused by the presence of finely divided suspended particles. If a beam of light is passed through a turbid sample, its intensity is reduced by scattering, and the quantity of light scattered is dependent upon the concentration, size and size distribution of the particles. The spectrophotometer measures the increased turbidity (i.e., the reduction of light in the intensity transmitted light), which is due to the increasing particle size resulting from the immunoagglutination reaction. This increased turbidity is a direct measure of the immunagglutination caused by the analyte or an indirect measure of the immunagglutination inhibition caused by the analyte. In nephelometry the intensity of the scattered light is measured, while in turbidimetry, the intensity of light transmitted through the sample is measured.

Turbidimetric assays involve measurement of the intensity of the incident beam as it passes through the sample. The light beam may pass through a suspension or be absorbed, reflected, or scattered by the particles. As a consequence, the intensity of light decreases as it is transmitted through the suspension. For non-absorbing particles the decrease in light intensity due to scattering is expressed as turbidity.

Nephelometric assays refer to the measurement of the light scattered at a defined angle of 0 from the incident beam when the incident beam is passed through the sample. In nephelometry the change in the intensity of the scattered light after a time is measured because the scattering species rapidly increase size. The scattered light is proportional to the initial antigen concentrations when measured in the presence of a fixed antibody-latex complex. Further explanations are described by J. A. Molina-Bolivar et al., Journal of Macromolecular Science, Part C-Polymer Review, 45:59-98, 2005.

The immunoassay method of the present disclosure works with all known agglutination tests with and without microparticles enhancement. Typically used within the present disclosure is a "microparticle-enhanced light scattering agglutionation tests" which is also called "particle-enhanced turbidimetric immunoassays" (PETIA). Agglutination-based immunoassays are routinely used in clinical diagnostics for the quantitation of serum proteins, therapeutic drugs and drugs of abuse on clinical chemistry analyzers, because they have the benefits of being quasi-homogeneous assays which do not require any separation or wash step. To enhance the optical detection between the specific analyte and an analyte specific binding partner in the reaction mixture, the analyte or the analyte specific binding partner is linked to suitable particles. Thereby, the analyte reacts and agglutinates with the particles which are coated with analyte specific binding partners. With increasing amount of analyte, the agglutination and the size of the complexes are increasing, leading further to a change of light scattering. The agglutinated particles are then determined by turbidimetric and nephelometric measurements.

The analyte comprises a mixture of particles of strong light scattering properties carrying at least one binding partner of high reactivity for the analyte and particles of weak light scattering properties carrying at least one binding partner of low reactivity for the analyte as described in EP 0898169. The particles of strong light scattering properties have a larger size and/or a higher refractive index than the particles of weak light scattering properties. The microparticle reagent for a microparticle enhanced light scattering immunoassay for determining the amount of an analyte, which comprises a mixture of microparticles of 30 to 600 nm in diameter, including particles of strong light scattering properties carrying at least one binding partner of high reactivity partner for the analyte and particles of weak light scattering properties carrying at least one binding partner of low reactivity for the analyte.

The material of the microparticles may be any inorganic, organic, or polymer material suitable for microparticle enhanced light scattering assays. The material of the microparticles may be any inorganic, organic, or polymer material suitable for microparticle enhanced light scattering assays. Such materials include for example selenium, carbon, gold; nitrides of carbon, silicium or germanium, e.g., Si3N4; oxides of iron, titanium or silicium, e.g., TiO2 or SiO2; and polymeric materials such as for example polystyrene, poly(vinyl chloride), epoxy resins, poly(vinylidene chloride), poly(alphanaphthyl methacrylate), poly(vinylnaphthalene), or copolymers thereof, in particular copolymers of styrene and a copolymerizable ethylenically unsaturated compound, e.g., styrene-(meth)acrylate co-polymers. Microparticles made of polymeric materials, as well as core-shell particles consisting of an inner core polymerized from styrene and an outer shell formed by copolymerization from styrene with a copolymerizable ethylenically unsaturated compound are particularly suitable. The majority of particle based assays employ latex particles, with the predominant type of being polystyrene.

The term "determining" as used herein means assessing, diagnosing, deciding, identifying, evaluating, quantifying or classifying a specific analyte in a sample from the change in the optical signal of the reaction mixture of a photometric assay based on turbidimetric or nephelometric measurements.

The term "amount" as used herein is encompasses the absolute amount of an analyte or the relative amount and/or concentration of said analyte and/or any value and/or parameter which may correlate thereto and/or may be derived therefore.

The term "analyte" according to the present disclosure encompasses any "in vitro diagnostic compound" such as, e.g., serum proteins, therapeutic drugs and drugs of abuse. Representative analytes include, but are not limited to antigens, haptens, antibodies, proteins, peptides, amino acids, hormones, steroids, cancer cell markers, tissue cells, viruses, vitamins, nucleic acids, pesticides, enzymes, enzyme substrates and enzyme cofactors. As used herein, an "analyte" or "specific analyte" refers to the substance whose presence and/or concentration in a sample is to be determined. The term "analyte" includes any substance for which there exists a specific reaction partner, e.g., a binding molecule or substance which specifically binds the analyte like antibodies, or a molecule which specifically reacts with the analyte, like enzymes), or for which a specific binding partner can be prepared.

The term "specific analyte" in the context of the present disclosure means that for each analyte in a sample to be measured, specific calibration curves and specific wavelengths and reaction times may be determined which are optimized for each specific analyte to quantify the concentration and which may differ from analyte to analyte.

The term "analyte specific reaction partner" as used herein is able to react with the specific analyte so as to form a reaction complex, like an antigen-antibody immunocomplex. Typical analyte specific reaction partners include, but are not limited to, binding proteins, antigens, antigen fragments, antibodies, antibody fragments, nucleic acids, receptors and particle enhanced binding partners. Such reaction partners specific for a given analyte may be obtained from commercial sources or may be prepared in accordance with standard procedures known to those skilled in the art. Examples of analyte specific reaction partner pairs include, but are not limited to, hapten:antibody, cell:antibody, biotin:avidin, hormone:receptor, polypeptide:antibody, antibody:antibody, oligonucleotide:complementary DNA or RNA. The term "analyte specific binding partner" can equally be used instead of "analyte specific reaction partner".

The term "antibody" as used herein refers to immunoglobulins that are produced in response to the detection of a foreign substance, and includes intact molecules as well as functional fragments thereof, such as Fab, F (ab') 2, and Fv. Antibodies that can be used as immunological binding partners in the assay of the present disclosure include polyclonal antibodies of any species, monoclonal antibodies of any species (including chimeric antibodies and/or recombinant antibodies). Because of their capacity of being produced identically in unlimited amounts, monoclonal antibodies or fragments thereof are generally typical.

The term "antigen" as used herein is characterized by its ability to be bound at the antigen-binding site of an antibody. The region of an antigen that is recognized by an antibody, and to which the antibody binds, is referred to as an "epitope." An antigen is a substance which is capable of inducing an immune response, i.e., antibody production, when introduced into an animal or human body. A hapten is a small molecule that can elicit an immune response only when attached to a large carrier such as a protein. The carrier may be one that also does not elicit an immune response by itself. Once the body has generated antibodies to a hapten-carrier adduct, the small-molecule hapten may also be able to bind to the antibody.

The term "sample" as used herein is refers to a sample of a body fluid selected from blood, i.e., whole blood, plasma, or serum, or urine, CSF, sputum or to a sample of separated cells or to a sample from a tissue or an organ of a respective individual. Samples of body fluids can be isolated by well-known techniques. Tissue or organ samples may be isolated from any tissue or organ by, e.g., biopsy. Separated cells may be isolated from the body fluids or the tissues or organs by separating techniques such as centrifugation or cell sorting. Typically, lysates from cell-, tissue- or organ samples are isolated from those cells, tissues or organs which express or produce the peptides referred to herein.

Nonlinear calibrations are used for tests whose absorbances at different concentrations form a nonlinear but reproducible plot. At least three and a maximum of six calibrators are required for calibration. A typical non-linear calibration type is the rodbard function. In addition, there are calibration types whose calibration curves are piecewise defined interpolation functions, like Spline.

Sensitivity, analytical sensitivity, lower detection limit (LDL), limit of blank (LOB), limit of detection (LOD) and limit of quantitation (LOQ) are terms used to describe the smallest concentration of a measurand that can be reliably measured by an analytical method. All of these terms are related but have distinct definitions (siehe Lit. clin biochem rev 2008, 29, 49). For example the term "analytical sensitivity" is defined as the slope of the calibration curve.

The term "lower detection limit" (LDL) as used herein is also called lower measuring range. A typical approach to estimate the LDL consists of measuring replicates, such as n=21, of a zero calibrator or blank sample, determining the mean value x and standard deviation (SD). The LDL is calculated as x+2SD or x+3SD. This method for the LDL determination is according to the method described by Kaiser (H. Kaiser, Fresenius Zeitschrift für analytische Chemie, 1965, 209, Nr. 1, pages 1-18).

The term "upper detection limit" (UDL) as used herein is also called the upper measuring range. The UDL is the highest amount of the analyte in a sample that can reliably be determined. In the present disclosure the UDL was determined by evaluating the linearity of the method and then selecting the highest concentration value within the linear range as the UDL. The method is said to be linear when the analyte recovery from a series of sample solutions (measured value) is proportional to the actual concentration of the analyte (true value) in the sample solutions (Arch Pathol Lab Med 2004, 128, pages 44-48). The form of the calibration curve, which can be parabolic or sigmoid-shaped, should not be confused with the linearity of the method which describes the relationship between the measured value and the true value. The calibration curve describes the relationship between signal and concentration.

It is common practice to determine the concentration of an analyte by using at least one "calibration curve" (also commonly referred to as standard curve or working curve) which has been preliminarily drawn by plotting the interrelation between the known concentrations of the analyte in the standard samples and the analytical measured values (optical signals) such as optical densities of the standard samples. When the calibration curve has an adequate linearity over a wider range in the region of quantitative analysis, the calibration curve can be prepared with a relatively smaller number of standard samples, which are near the upper limit, lower limit and in the intermediate point in the determination range of the quantitative analysis. In practice, however, there are many calibration curves which are not linear in general. The calibration curve of turbidimetric or nephelometric, prepared from the absorbance of a specific wavelength, may have a nonlinear S-shape calibration curve where the sensitivity is deteriorated at the concentration near zero, and is saturated at a higher concentration side. The determination of the S-shape calibration requires a multipoint calibration where the use of the standard samples of the plurality of the concentrations is obliged.

When generating a calibration curve for an agglutination assay based on measurements of the turbidity of the reaction mixture, the selection of the wavelength plays, beside the reaction time, a crucial role for the slope (analytical sensitivity) of the curve and the achievable upper measuring range. The selection of the one wavelength and a corresponding reaction time for the signal calculation aimed at the generation of a calibration curve may be a compromise between analytical sensitivity and upper measuring range.

An embodiment of the present disclosure is to generate a calibration curve at at least one wavelength and reaction time for the specific analyte of a sample to be determined and depositing the measurement results in a data management system of the instrument platform.

Afterwards the optical signal for the specific analyte in the sample to be determined is measured simultaneously at the wavelength used for the determination of the analyte and at least at an additional specific wavelength used for the detection of the prozone effect over the complete reaction time. This (or these) additional specific wavelength (s) is different to the wavelength used for the determination of the analyte.

It is an embodiment of the present disclosure that the difference between the wavelengths used for the determination of the analyte and at least at an additional specific wavelength used for the detection of the prozone effect is higher than 10 nm.

Typically, this (or these) additional specific wavelength (s) shows a difference of 5 nm, 10 nm, or 20 nm. In specific situations, the difference between the wavelength used for the determination of the analyte and at least at an additional specific wavelength used for the detection of the prozone effect may be even higher than 20 nm.

The term "wavelength used for the determination of the analyte", also called main wavelength, as well as the at least one wavelength for the detection of the prozone effect as used herein refers to the wavelengths generated with a multiple wavelength photometer known in the art. Common photometers are spectrophotometers or turbidimeters for turbidimetric immunoassays and nephelometers for nephelometric immunoassays. The detection of these assays on the Roche cobas c instruments is based on a photometer with a tungsten halogen lamp as irradiation source, a grating for generating monochromatic light and photodiode array (12 diodes yielding 12 wavelengths between 340 and 800 nm) as detector. A photometer, e.g., the Roche cobas c 311 analyzer has the ability to measure 12 wavelengths between 300 nm to 800±2 nm simultaneously. Typically used are the wavelengths 340, 376, 415, 450, 480, 505, 546, 570, 600, 660, 700, 800±2 nm. The method of the present disclosure is especially advantageous if used in automated analyzers, such as the Roche cobas c 311 analyzer, having the capability of measuring multiple wavelengths simultaneously. Depending on the architecture of the chosen spectrophotometer and the available wavelengths, which may differ from device to device, one or more specific wavelengths are selected out of multiple wavelengths. The measurements are typically performed at a defined temperature, typically between 20 and 40 degree Celsius, more typically at 37° C.

An embodiment of the present disclosure is that a second or a further wavelength is optional used for correction/blanking purposes. This further wavelength is determined as a blank value for the correction of interferences and compensation of photometric noise, also known as bichromatic measurement (clin. Chem. 1979, 25, 1482-1484). Typically a subtraction of the signal at the correction wavelength from the signal at the main wavelength is performed.

The term "optical signal" as used herein describes the signal that is obtained by performing an absorbance measurement of the reaction mixture. The optical signal may be an absorbance value in case of turbidimetric assays or a scattered light signal for nephelometric assays. The optical signal for the specific analyte in the sample can simultaneously be measured in the reaction mixture at multiple wavelengths, typically in one run over the entire reaction time.

The term "simultaneously" as used in the present disclosure, may imply a time delay smaller 60× seconds, e.g., a time delay smaller 10× seconds, typically smaller 1× second, most typically smaller 1 ms, or even smaller 0.1× ms. Most typically, the term "simultaneously" means no time delay.

The term "prozone effect" also called high-dose Hook effect or antigen excess effect as used herein, is a phenomenon where the assay response at high analyte concentrations decrease and results in falsely lower measured values of the analyte.

An embodiment of the present disclosure is to calculate the "reaction rate ratio R by using the signals obtained at the wavelength used for the detection of the prozone effect.

The term "reaction rate ratio R" as used herein is defined:

$R$=[reaction rate at time period 2/reaction rate at time period 1]×100 with reaction rate at time period 2=[signal(time point4)−signal(time point3)]/[time point4−time point3] and reaction rate at time period 1=[signal(time point2)−signal(time point1)]/[time point2−time point1].

By comparison of the calculated ratio value R with predetermined limit values it is judged if a prozone effect is present in the sample. A hook effect according to the present disclosure can be detected using the commercially available spectrophotometric laboratory tests on the corresponding instrument platform without applying pre-analytical sample dilution treatment and/or changing the assay procedure by analyte re-addition.

An embodiment of the present disclosure is that if a prozone effect is present after diluting the sample, the measurement of a sample is automatically repeated.

It is a further embodiment of the present disclosure that in case that no prozone effect is present in the sample, the determined amount of specific analyte in the sample is a reportable result.

Furthermore, it is an embodiment of the present disclosure that additional signal(s) are optionally measured at the wavelength used for determination of the analyte and/or at the wavelength used for the calculation of R and/or at another wavelength, are assessed by comparison with predetermined limit values before calculating and judging the presence of a Hook effect based on the reaction rate ratio R. Such a predetermined limit value according to the present disclosure, may be defined for a signal change in a certain time period, for deciding if a sample with extremely high reaction rate is immediately categorized, e.g., as Hook sample or for neglecting samples with extremely low reaction rates from a prozone check and classifying such samples directly, e.g., as non-Hook samples.

The term "predetermined limit" or "threshold value" as used herein, is used for defined signal changes in a certain time period, also expressed as reaction rate, or for defined reaction rate ratios, as described above in the formula for R. The predetermined limit may also be an absorbance value taken at a certain time point. A predetermined limit is applied to the method of the disclosure for the detection of a prozone effect. The selection of the predetermined limits is performed empirically during the assay development by comparing non-Hook-with Hook samples.

A further embodiment of the present disclosure is that specific measurement conditions comprising reaction times, calibration points, calibration mode and the assay type are additional applied to the measurement protocol according the present disclosure.

The term "reaction time" as used herein is in case of endpoint assays the time period between the first (or initial) and second (or final) measurement of the optical signal which is used for the calculation of a signal value hereof. The first (or initial) measurement is performed before or shortly after the final reagent is added to the reaction mixture. In case of kinetic measurements the reaction time may be the time period used for the calculation of the value expressing the absorbance change per time. The "reaction time" may be identical or shorter that the complete reaction time. The complete reaction time is the time that the reaction mixture, composed of sample and analyte specific assay reagents, is allowed to react after their mixing.

The term "complete reaction time" as used herein is the time period of measuring a specific analyte at a plurality of wavelengths. Samples are simultaneously measured at the 12 different wavelengths available on the Roche cobas c analyzer. The typical complete reaction time of the present immunoassay time varies between 1 and 20 minutes. Typically, the complete reaction time of a multiple wavelength spectrophotometer photometer typically is around 10 minutes. It is an embodiment of the present disclosure that the optical signals of the specific analyte are measured during the complete reaction time.

The term "number of calibration points" as used herein is the number of calibrators also called sample standards used to generate the calibration curve.

The term "calibration mode" as used herein refers to the determination of a valid relation between the measured signal [absorbance or (for rate assays) a rate of change in absorbance] and the concentration of the analyte of interest. The graphical representation of such a signal/concentration relation is the calibration curve also referred to as working curve. The analyzers use different types of mathematical models to describe this relation. These mathematical models are referred to as calibration types or calibration modes. Two basic modes of calibration exist, the linear and non-linear calibration modes. Linear calibrations are used for tests when the absorbance readings plotted against calibrator concentrations lie on a straight line. If a linear calibration is based on two calibrator measurements, it is termed linear two-point calibration. If a calibration is based on more than two calibrators, it is termed linear multipoint calibration. A multipoint calibration is typically used for non-linear calibrations.

The term "assay type" as used herein refers to two fundamental types of photometric assays on analyzers: endpoint assays and rate assays. Measurements are taken by the photometer at specific time points. If measurements are taken after the reactions are completed, the absorbance (or turbidity) is an indicator of the sample component's concentration. These are called endpoint assays. For rate assays, the rate of the reaction rate (rate of change in absorbance) is proportional to the concentration of the sample component being analyzed. Measurements are taken as the reaction proceeds. There are also modifications of these two techniques possible in this instrument, as well as a combination of the two.

A further aspect of the present disclosure is a method for determination of the amount of albumin in a sample which may show a prozone effect, by photometric assays, wherein the specific analyte is quantified from the change in the optical signal of the reaction mixture after the interaction of the analyte with analyte specific assay reagents.

A calibration curve at at least one wavelength and reaction time is generated for albumin in a sample to be determined and depositing the measurement results in a data management system of the instrument platform.

The optical signal for albumin in the sample is measured simultaneously to be determined at the wavelength used for the determination of the analyte and at least at an additional specific wavelength used for the detection of the prozone effect over the complete reaction time.

The reaction rate ratio R is calculated by using the signals obtained at the wavelength used for the detection of the prozone effect $R$=[reaction rate at time period 2/reaction rate at time period 1]×100 with reaction rate at time period 2=[signal(time point4)−signal(time point3)]/[time point4−time point3] and reaction rate at time period 1=[signal(time point2)−signal(time point1)]/[time point2−time point1].

If a prozone effect is present in the sample is judged by comparison of the calculated ratio value R with predetermined limit values, the amount of albumin is quantified by comparison of the optical signal obtained at the wavelength used for the determination of the analyte with the calibration curve.

An embodiment of the present disclosure is that in some cases the wavelength used for the determination of albumin is the same wavelength which is used for the detection of the prozone effect. In this case additional limits such as such as additional signals and reference values are measured at the wavelength used for the determination of the analyte and/or wavelength used for the detection of the prozone effect.

It is therefore an embodiment of the present disclosure that optionally further limits may be defined and applied to each measurement related with the determination of the amount of albumin which decides how to proceed before the R calculation f judging the presence of a Hook effect based on the reaction rate ratio R. These limits are reference values for signals which are measured at the wavelength used for the determination of the analyte, and/or at the wavelength used for the detection of the prozone effect, and/or other wavelengths. An example for such a limit may be defined for a signal change in a certain time period, for neglecting samples with extremely low reaction rates from a prozone check and classifying such samples directly as non-Hook samples. A further example for such a limit may be defined for a signal change in a certain time period, for deciding if a sample with extremely high reaction rate is immediately categorized as Hook sample or if the judgment is performed after the calculation of the reaction rate ratio R.

A further aspect of the present disclosure is the use of specific measurement conditions additional applied to the measurement protocol for spectrophotometric-based laboratory tests for determining the amount of the specific analyte in a sample which may show a prozone effect, by photometric assays, comprising wavelengths for measurement, reaction times, calibration points, and calibration mode.

Instrument platform using a commercially available spectrophotometric laboratory tests for determining the amount of the specific analyte in a sample which may show a prozone effect, by photometric assays, wherein the data management system of the instrument platform is able to process data of reaction times, calibration points, calibration mode, wavelengths, for selecting the best fitting calibration curve. Additional corrections of the measurement results according to the present disclosure comprising wavelengths for measurement, reaction times, calibration mode, number of calibration point are performed and offsetted against each other.

In order that the embodiments of the present disclosure may be more readily understood, reference is made to the following examples, which are intended to illustrate the disclosure, but not limit the scope thereof.

Example 1: Prozone Detection for the CRP Assay 1.1 Instrument:

The Roche cobas c 311 analyzer (Roche Diagnostics GmbH), which has a multiple wavelength spectrophotometer as detection unit, was used for the experiments. The instrument automatically pipettes the sample and the assay reagents into reaction cells. Up to 3 different reagents, R1, R2 and R3, may be added to the sample. The instrument uses a tungsten halogen lamp as irradiation source (12 V/50 W) and measures the absorbance simultaneously at 12 different wavelengths (at 340, 376, 415, 450, 480, 505, 546, 570, 600, 660, 700 and 800±2 nm) with a photodiode array consisting of 12 photodiodes. The optical path length is 5.6 mm and the optical range of the detector is 0.0000-3.0000 absorbance. For each reaction cell, a water-blank is measured and then absorbance readings are taken 57 times in 10 minutes, here also called the complete reaction time, thus yielding a total of 57 measure points for the absorbance at each wavelength, also called photometric points or assay points. The concentration can be calculated by using at least one of these measurement points. There are two fundamental types of photometric assays on this instrument: endpoint assays and rate assays. The measurements are performed at 37 degree Celsius.

1.2 Procedure for the CRP-Assay Using the Standard Approach:

Roche's CRP L3 test (CRPL3, Cat. No. 04956842), a particle-enhanced immunoturbidimetric assay, was selected for this study. Human CRP agglutinates with latex particles coated with monoclonal anti-CRP antibodies; the aggregates are determined turbidimetrically. Reagents for all Roche tests are provided in Roche cobas c packs. These cassettes contain from one to three specially designed reagent bottles and have barcode labels with detailed reagent and other test-related information. For CRP L3 tests two reagents are used in the cassette: R1 (TRIS buffer with bovine serum albumin and preservatives) and R2 (Latex particles coated with anti-CRP (mouse) in glycine buffer, immunoglobulins (mouse) and preservative). The procedure described in the package insert document from the CRP L3 test was used as standard method.

1.2.1 Pipetting Scheme:

2 µL sample and 150 µL assay buffer (R1) were added subsequently to the reaction cell, followed by the addition of the latex reagent (R2, 48 µL), diluted with 24 µl diluent (water), and mixing of the reaction mixture.

1.2.2 Conditions for the Generation of the Calibration Curve:

For the measurements 570 nm was used as main wavelength and 800 nm as correction wavelength. The assay type was a two-point-end assay. A two-point-end assay is an end-point-assay which performs a sample blank. Here two absorbance readings at two different measure points are considered: the first reading is usually taken before or shortly after the final reagent is added; the second reading is taken at any time point after the final reagent was added. The absorbance value for the calibration curve and therefore for the concentration calculation is obtained by subtraction of the second reading from the first reading. For CRP L3 the first reading is at measure point 8 and means shortly after the final reagent addition, and the second reading at measure point 18, which corresponds to a reaction time of 2.0 minutes. For the generation of the calibration curve 6 standards from Roche (Cat. No. 11355279) are measured as duplicates with spline as calibration type, which fits the ranges between the data points of the measured calibrators approximated by third degree polynomials so that a smooth calibration curve is obtained.

1.2.3 Conditions for the Detection of the Prozone Effect:

For the detection of the prozone effect the reaction rate method is used (see also FIGS. 2, 3 and 4). Firstly, 2 different limits are applied to the measurement: the signal differences between prozone measure point 1 ($pmp_1$) and prozone measure point 2 ($pmp_2$) and signal differences between prozone measure point 3 ($pmp_3$) and prozone measure point 4 ($pmp_4$) are calculated. These calculated signal (absorbance) differences are compared with predetermined limit values, 950 for (Apmp2−Apmp1) and 100 for (Apmp4−Apmp3) respectively (see column 8 and 9 of the prozone settings in FIG. 4 and in the table below). Samples with calculated signal differences being below these limits are directly classified as non-Hook samples. However, if the calculated signal differences of a sample are above these limits, a prozone check is performed by calculating the prozone check values PC according to FIG. 3: the ratio of the reaction rate at the end of the reaction ($v_{(pmp3,pmp4)}$, see column 5 and 6 of the prozone settings in FIG. 4 and in the table below) and the reaction rate at the beginning of the reaction ($v_{(pmp1,pmp2)}$, see column 3 and 4 of the prozone settings in FIG. 4 and in the table below), expressed as percent, is calculated in order to obtain the prozone check value PC. For each assay the specific PC ranges, defined as range between a lower limit (see column 1 in FIG. 4 and in the table below) and an upper limit (see column 2 in FIG. 4 and in the table below), indicating a prozone effect, are stored in the assay settings, and automatically compared with the PC values obtained after the measurement of each sample: if the sample shows a PC value is inside the lower and upper limit (4-15), then the sample is flagged as Hook sample. The settings for the prozone check for CRP L3 are depicted in the table below (see also FIG. 4 for detailed description):

Used wavelength for prozone check, additional limits and analyte quantitation: 570 nm (800 nm correction wavelength):

| Prozone check value (PC) settings: Wavelength: 570-800 nm | | | | | | | Additional limits settings: Wavelength: 570-800 nm | |
|---|---|---|---|---|---|---|---|---|
| Lower limit | Upper limit | pmp1 | pmp2 | pmp3 | pmp4 | Comp. | 0 | 0 |
| 4 | 15 | 8 | 11 | 16 | 19 | inside | 950 | 100 |

1.3 Procedure for the CRP-Assay According to the Disclosure:

The reagents used for these experiments were identical to those used for the standard method: see point 1.2. The procedure described in the package insert document from the CRP L3 test was used with exception of the method for the detection of a prozone effect.

1.3.1 Measurement Conditions:

Pipetting scheme: is identical to pipetting scheme of standard method depicted in point 1.2.1. Conditions for the generation of the calibration curve: are identical to calibration conditions used in the standard method depicted in point 1.2.2.

1.3.2 Conditions for the Detection of the Prozone Effect According to the Disclosure:

For the detection of the prozone effect the method of the disclosure also uses an analysis of the reaction rate, however, using other wavelength(s) than those used for the quantitation of the analyte. Firstly, 2 different limits are applied to the measurement: the signal differences between prozone measure point 7 (pmp7) and prozone measure point 8 (pmp8) and signal differences between prozone measure point 9 (pmp9) and prozone measure point 10 (pmp10) at the wavelength 660 nm (800 nm correction wavelength) are calculated. These calculated signal (absorbance) differences are compared with predetermined limit values, 500 for (Apmp8−Apmp7) and 200 for (Apmp10−Apmp9) respectively (see column 8 and 9 in the table below). Samples with calculated signal differences being below these limits are directly classified as non-Hook samples.

However, if the calculated signal differences of a sample are above these limits, a prozone check is performed by calculating the reaction rate ratio R from signals obtained at the wavelength used for the detection of the prozone effect:

$$R=[\text{reaction rate at time period 2/reaction rate at time period 1}]\times 100 \text{ with reaction rate at time period 2}=[\text{signal(time point4)}-\text{signal(time point3)}]/[\text{time point4}-\text{time point3}] \text{ and reaction rate at time period 1}=[\text{signal(time point2)}-\text{signal(time point1)}]/[\text{time point2}-\text{time point1}].$$

Time point 4: is prozone measure point 4 pmp4 and identical with measure point 4; time point 3: is prozone measure point 3 pmp3 and identical with measure point 3; time point 2: is prozone measure point 2 pmp2 and identical with measure point 2; time point 1: is prozone measure point 1 pmp1 and identical with measure point 1; see also table below columns $3^{rd}$ to $6^{th}$.

For each assay the specific and predetermined R ranges, defined as range between a predetermined lower limit (see column 1 in the table below) and a predetermined upper limit (see column 2 in the table below), indicating a prozone effect, are stored in the assay settings, and automatically compared with the R values obtained after the measurement of each sample: if the sample shows a R value which is inside (according to the $7^{th}$ column in table below) the lower and upper limit (8-17.2), then the sample is flagged as Hook sample.

The settings for the prozone check for CRP L3 are depicted in the table below:

Used wavelength for prozone check: 660 nm (800 nm correction wavelength);

Used wavelength for the additional limits: 660 nm (800 nm correction wavelength);

Used wavelength for analyte quantitation: 570 nm (800 nm correction wavelength).

| Prozone check value parameters/settings: Wavelength: 660-800 nm | | | | | | | Additional limits: Wavelength: 660-800 nm | |
|---|---|---|---|---|---|---|---|---|
| Lower limit | Upper limit | pmp1 | pmp2 | pmp3 | pmp4 | Comp. | Min. limit Apmp8–Apmp7 | Min. limit Apmp10–Apmp9 |
| 8 | 17.2 | 8 | 10 | 17 | 20 | inside | 500 (pmp8: 10 pmp7: 8) | 200 (pmp10: 20 pmp9: 17) |

Optionally, the wavelengths to be used for each of the additional limits may be different. In this case good results were obtained by using the same wavelength for both additional limits.

1.4 Results for the CRP-Assay Using the Standard and the Approach According to the Disclosure:

The result overview is depicted in FIGS. 5A and 5B. The application of the new approach to the CRP test shows an improved differentiation between Hook- and non-Hook samples by a factor of 2.7. The new approach affords minimal implementation efforts; the application of the approach does not need any changes of reagents and their formulations. For its application on the Roche cobas c analyzer only the input windows in the software are to be adapted: extension by the additional setting of the measurement wavelength and the possibility to make an input of lower/upper limit values with decimal units, e.g., 17.2 instead of only 17.

Example 2: Prozone Detection for the Ferritin Assay 2.1 Instrument: See Point 1.1.

2.2 Procedure for the Ferritin-Assay Using the Standard Approach:

Roche's Ferr4 test (Ferr4, Cat. No. 04885317), a particle-enhanced immunoturbidimetric assay, was selected for this study. Human ferritin agglutinates with latex particles coated with monoclonal anti-ferritin antibodies; the aggregates are determined turbidimetrically. Reagents for all Roche tests are provided in Roche cobas c packs. These cassettes contain from one to three specially designed reagent bottles and have barcode labels with detailed reagent and other test-related information. For Ferr4 tests two reagents are used in the cassette: R1 (TRIS buffer, pH 7.5, immunoglobulins (rabbit), preservative, stabilizers) and R3 (Aqueous matrix containing latex particles coated with anti-human ferritin antibodies (rabbit), preservative, stabilizers). The procedure described in the package insert document from the Ferr4 test was used as standard method.

2.2.1 Pipetting Scheme:

10 µL sample and 80 µL assay buffer (R1) were added subsequently to the reaction cell, followed by the addition of 80 µL of the latex reagent (R3) and mixing of the reaction mixture.

2.2.2 Conditions for the Generation of the Calibration Curve:

For the measurements 570 nm was used as main wavelength and 800 nm as correction wavelength. The assay type was a two-point-end assay. A two-point-end assay is an end-point-assay which performs a sample blank. Here two absorbance readings at two different measure points are considered: the first reading is usually taken before or shortly after the final reagent is added; the second reading is taken at any time point after the final reagent was added. The absorbance value for the calibration curve and therefore for the concentration calculation is obtained by subtraction of the second reading from the first reading. For CRP L3 the first reading is at measure point 24 and means shortly after the final reagent addition, and the second reading at measure point 57, which corresponds to a reaction time of 5.1 minutes. For the generation of the calibration curve 6 standards from Roche (Cat. No. 11355279) are measured as duplicates with spline as calibration type, which fits the ranges between the data points of the measured calibrators approximated by third degree polynomials so that a smooth calibration curve is obtained.

2.2.3 Conditions for the Detection of the Prozone Effect:

For the detection of the prozone effect the reaction rate method is used (see also FIGS. 2, 3 and 4). Firstly, one limit is applied to the measurement: the signal difference between prozone measure point 1 ($pmp_1$) and prozone measure point 2 ($pmp_2$) is calculated. This calculated signal (absorbance) difference is compared with the predetermined limit value, which is 1000 for (Apmp2−Apmp1) (see column 8 of the prozone settings in FIG. 4 and in the table below). Samples with calculated signal difference being below this limit are directly classified as non-Hook samples. However, if the calculated signal difference of a sample is above this limit, a prozone check is performed by calculating the prozone check values PC according to FIG. 3: the ratio of the reaction rate at the end of the reaction ($v_{(pmp3,pmp4)}$, see column 5 and 6 of the prozone settings in FIG. 4 and in the table below) and the reaction rate at the beginning of the reaction ($v_{(pmp1,pmp2)}$, see column 3 and 4 of the prozone settings in FIG. 4 and in the table below), expressed as percent, is calculated in order to obtain the prozone check value PC. For each assay the specific PC ranges, defined as range between a lower limit (see column 1 in FIG. 4 and in the table below) and an upper limit (see column 2 in FIG. 4 and in the table below), indicating a prozone effect, are stored in the assay settings, and automatically compared with the PC values obtained after the measurement of each sample: if the sample shows a PC value is inside the lower and upper limit (0-10), then the sample is flagged as Hook sample. The settings for the prozone check for Ferr4 are depicted in the table below (see also FIG. 4 for detailed description):

Used wavelength for prozone check, additional limits and analyte quantitation: 570 nm (800 nm correction wavelength):

| Prozone check value parameters/settings: Wavelength: 570-800 nm | | | | | | | Additional limits: Wavelength: 570-800 nm | |
|---|---|---|---|---|---|---|---|---|
| Lower limit | Upper limit | pmp1 | pmp2 | pmp3 | pmp4 | Comp. | 0 | 0 |
| 0 | 10 | 25 | 29 | 43 | 47 | inside | 1000 | — |

2.3 Procedure for the Ferritin-Assay According to the Disclosure:

The reagents used for these experiments were identical to those used for the standard method: see point 2.2. The procedure described in the package insert document from the Ferr4 test was used with exception of the method for the detection of a prozone effect.

2.3.1 Measurement Conditions:

Pipetting scheme: is identical to pipetting scheme of standard method depicted in point 2.2.1. Conditions for the generation of the calibration curve: are identical to calibration conditions used in the standard method depicted in point 2.2.2.

2.3.2 Conditions for the Detection of the Prozone Effect According to the Disclosure:

For the detection of the prozone effect the method of the disclosure also uses an analysis of the reaction rate, however, using other wavelength(s) than those used for the quantitation of the analyte. Firstly, one limit is applied to the measurement: the signal difference between prozone measure point 7 (pmp7) and prozone measure point 8 (pmp8) at the wavelength 505 nm (800 nm correction wavelength) is calculated. This calculated signal (absorbance) difference is compared with the predetermined limit value, which is 1000 for (Apmp8−Apmp7) respectively (see column 8 in the table below). Samples with calculated signal differences being below this limit are directly classified as non-Hook samples. However, if the calculated signal difference of a sample is above this limit, a prozone check is performed by calculating the reaction rate ratio R from signals obtained at the wavelength used for the detection of the prozone effect:

$R$=[reaction rate at time period 2/reaction rate at time period 1]×100 with reaction rate at time period 2=[signal(time point4)−signal(time point3)]/[time point4−time point3] and reaction rate at time period 1=[signal(time point2)−signal(time point1)]/[time point2−time point1].

Time point 4: is prozone measure point 4 pmp4 and identical with measure point 4; time point 3: is prozone measure point 3 pmp3 and identical with measure point 3; time point 2: is prozone measure point 2 pmp2 and identical with measure point 2; time point 1: is prozone measure point 1 pmp1 and identical with measure point 1; see also table below columns $3^{rd}$ to $6^{th}$.

For each assay the specific and predetermined R ranges, defined as range between a predetermined lower limit (see column 1 in the table below) and a predetermined upper limit (see column 2 in the table below), indicating a prozone effect, are stored in the assay settings, and automatically compared with the R values obtained after the measurement of each sample: if the sample shows a R value which is inside (according to the $7^{th}$ column in table below) the lower and upper limit (between −5 and 5), then the sample is flagged as Hook sample.

The settings for the prozone check for the FERR4 are depicted in the table below:

Used wavelength for prozone check: 505 nm (800 nm correction wavelength);

Used wavelength for the additional limits: 505 nm (800 nm correction wavelength);

Used wavelength for analyte quantitation: 570 nm (800 nm correction wavelength).

| Prozone check value parameters/settings: Wavelength: 505-800 nm | | | | | | | Additional limits: Wavelength: 505-800 nm | |
|---|---|---|---|---|---|---|---|---|
| | | | | | | | Min. limit | Min. limit |
| Lower limit | Upper limit | pmp1 | pmp2 | pmp3 | pmp4 | Comp. | Apmp8-Apmp7 | Apmp10-Apmp9 |
| −5 | 5 | 24 | 26 | 41 | 43 | inside | 1000 (pmp8: 26 pmp7: 24) | — |

2.4 Results for the Ferritin-Assay Using the Standard and the Approach According to the Disclosure:

The result overview is depicted in FIGS. 6A and 6B. The application of the new approach of Ferritin test shows an improved differentiation between Hook- and non-Hook samples by a factor of 1.8. The new approach affords minimal implementation efforts; the application of the approach does not need any changes of reagents and their formulations. For its application on the Roche cobas c analyzer only the input windows in the software are to be adapted: extension by the additional setting of the measurement wavelength.

Example 3: Prozone Detection for the Albumin Assay 3.1 Instrument: See Point 1.1.

3.2 Procedure for the Albumin-Assay Using the Standard Approach:

Roche's Albumin test (ALBT2, Cat. No. 04469658), an immunoturbidimetric assay, was selected for this study. This test is used to determine albumin in urine samples. Human albumin reacts with polyclonal anti-albumin antibodies forming antigen/antibody complexes; the aggregates are determined turbidimetric ally.

Reagents for all Roche tests are provided in Roche cobas c packs. These cassettes contain from one to three specially designed reagent bottles and have barcode labels with detailed reagent and other test-related information. For ALBT2 tests three reagents are used in the cassette: R1 (TRIS buffer: 50 mmol/L, pH 8.0, PEG: 4.2%, EDTA: 2.0 mmol/L, preservative), R2 (Polyclonal anti-human albumin antibodies (sheep): dependent on titer, TRIS buffer: 100 mmol/L, pH 7.2, preservative) and R3 (Albumin in diluted serum (human), NaCl: 150 mmol/L, phosphate buffer: 50 mmol/L, pH 7.0, preservative). Reagent R3 is used to perform the antigen excess check by the antigen readdition method. The procedure described in the package insert document from the ALBT2 test was used as standard method.

3.2.1 Pipetting Scheme:

6 μL sample and 100 μL assay buffer (R1) were added subsequently to the reaction cell, followed by the addition of 20 μL of the antibody reagent (R2), and mixing of the reaction mixture. Afterwards 6 μL of reagent R3 (antigen excess check), diluted with 20 μl diluent (water), was added to the reaction mixture and mixed.

3.2.2 Conditions for the Generation of the Calibration Curve:

For the measurements 340 nm was used as main wavelength and 700 nm as correction wavelength. The assay type was a two-point-end assay. A two-point-end assay is an end-point-assay which performs a sample blank. Here two absorbance readings at two different measure points are considered: the first reading is usually taken before or shortly after the final reagent is added; the second reading is taken at any time point after the final reagent was added. The absorbance value for the calibration curve and therefore for the concentration calculation is obtained by subtraction of the second reading from the first reading. For ALBT2 the first reading is at measure point 6 and means shortly before the final reagent (R2) addition, and the second reading at measure point 15, which corresponds to a reaction time of 1.8 minutes. For the generation of the calibration curve 6 standards from Roche (Cat. No. 03121305) are measured as duplicates with RCM as calibration type (Rodbard fit function).

3.2.3 Conditions for the Detection of the Prozone Effect:

For the detection of the prozone effect the antigen re-addition method is used. After completion of the assay (between measure points 23 and 24) the albumin reagent (R3) is added to the assay mixture and the additional change in the signal is interpreted. Typically, for Hook samples the signal decreases, and for non-Hook samples the signal increases. The wavelengths used for the analyte quantitation and for the signal analysis after the antigen-re-addition are identical.

3.3 Procedure for the Albumin-Assay According to the Disclosure:

The reagents used for these experiments were identical to those used for the standard method: see point 3.2. The procedure described in the package insert document from the ALBT2 test was used with exception of the prozone check method.

3.3.1 Measurement Conditions:

Pipetting scheme: is identical to pipetting scheme of standard method depicted in point 3.2.1. Conditions for the ratio R from signals obtained at the wavelength used for the detection of the prozone effect (505 nm main wavelength, 700 nm correction wavelength):

$R$=[reaction rate at time period 2/reaction rate at time period 1]×100 with reaction rate at time period 2=[signal(time point4)−signal(time point3)]/[time point4−time point3] and reaction rate at time period 1=[signal(time point2)−signal(time point1)]/[time point2−time point1].

Time point 4: is prozone measure point 4 pmp4 and identical with measure point 4; time point 3: is prozone measure point 3 pmp3 and identical with measure point 3; time point 2: is prozone measure point 2 pmp2 and identical with measure point 2; time point 1: is prozone measure point 1 pmp1 and identical with measure point 1; see also table below columns $3^{rd}$ to $6^{th}$.

For each assay the specific and predetermined R ranges, defined as range between a predetermined lower limit (see column 1 in the table below) and a predetermined upper limit (see column 2 in the table below), indicating a prozone effect, are stored in the assay settings, and automatically compared with the R values obtained after the measurement of each sample: if the sample shows a R value which is outside (according to the $7^{th}$ column in table below) the lower and upper limit (between −5 and 42), then the sample is flagged as Hook sample.

The settings for the prozone check for the albumin assay are depicted in the table below:

Used wavelength for prozone check: 505 nm (700 nm correction wavelength);
Used wavelength for the additional limits: 340 nm (700 nm correction wavelength);
Used wavelength for analyte quantitation: 340 nm (700 nm correction wavelength).

| Prozone check value parameters/settings: Wavelength: 505-700 nm | | | | | | | Additional limits: Wavelength: 340-700 nm | | |
|---|---|---|---|---|---|---|---|---|---|
| Lower limit | Upper limit | pmp1 | pmp2 | pmp3 | pmp4 | Comp. | Min. limit Apmp8− Apmp7 | Min. limit Apmp10− Apmp9 | Max. limit Apmp6− Apmp5 |
| −5 | 42 | 6 | 10 | 14 | 22 | outside | — | — | 2500 (pmp6: 23 pmp5: 8) | generation of the calibration curve: are identical to calibration conditions used in the standard method depicted in point 3.2.2.

3.3.2 Conditions for the Detection of the Prozone Effect According to the Disclosure:

a) For the detection of the prozone effect the method of the disclosure also uses an analysis of the reaction rate, however, using other wavelength(s) than those used for the quantitation of the analyte. Firstly, one limit is applied to the measurement: the signal difference between prozone measure point 5 (pmp5) and prozone measure point 6 (pmp6) at the wavelength 340 nm (700 nm correction wavelength) is calculated. This calculated signal (absorbance) difference is compared with the predetermined limit value, which is 2500 for (Apmp6−Apmp5) (see column 10 in the table below). Samples with calculated signal differences being above this limit are directly classified as Hook samples. However, if the calculated signal difference of a sample is below this limit, a prozone check is performed by calculating the reaction rate 3.4 Results for the Albumin-Assay Using the Standard and the Approach According to the Disclosure:

The result overview is depicted in FIGS. 7A and 7B. The application of the new approach of ALBT2 test allows clear differentiation between Hook- and non-Hook-samples by applying the reaction rate method. As consequence, the avoidance of a second antigen addition leads to cost and time savings. The new approach affords minimal implementation efforts; the application of the approach does not need any changes of reagents and their formulations. For its application on the Roche cobas c analyzer only the input windows in the software are to be adapted and/or slightly modified: extension by the additional setting of the measurement wavelength and an additional setting is necessary for a limit (max. limit) which may be defined as a signal change in a certain time period, for deciding if a sample with extremely high reaction rate is immediately categorized as Hook sample or if the judgment is performed after the calculation of the reaction rate ratio R.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

What is claimed is:

1. A computer-implemented method, performed by a data management system of a photometer instrument platform including a processor and a memory, for determining an amount of a specific analyte in a sample which may show a prozone effect by photometric assays, wherein the specific analyte is quantified from a change in an optical signal of a reaction mixture after interaction of the specific analyte with analyte specific assay reagents, wherein the data management system is in communication with the photometer instrument platform which further includes at least one pipette and at least one reaction cell, wherein the data management system controls the operation of the pipette, the method comprising the following steps:
   a) automatically pipetting a reaction mixture comprising a sample and an assay reagent into at least one reaction cell to obtain measurement results;
   b) generating a calibration curve using the data management system for at least one wavelength and reaction time for the specific analyte of the sample to be determined;
   c) depositing the measurement results as an input to the data management system;
   d) measuring simultaneously an optical signal from a first wavelength and at least one second wavelength in the sample over a complete reaction time using a photometer system, wherein the first wavelength is used for the determination of the specific analyte in the sample, and the second wavelength is used for the determination of the prozone effect in the sample;
   e) calculating a reaction rate ratio R using the data management system by using the signal obtained at the at least one second wavelength R=[reaction rate time period 2/reaction rate at time period 1]×100 with reaction rate at time period 2=[signal(time point4)−signal(time point3)]/[time point4−time point3] and reaction rate at time period 1=[signal(time point2)−signal(time point1)]/[time point2−time point1];
   f) using the data management system to determine whether a prozone effect is present in the sample by comparison of the R value calculated in step (e) with predetermined limit values;
   g) using the data management system to quantify an amount of the specific analyte by comparison of the optical signal obtained at the first wavelength using the photometer system with the calibration curve; wherein
   h) if step (f) determines that a prozone effect is not present, then reporting the amount quantified in step (g) as the amount of specific analyte in the sample, and if step (f) determines that a prozone effect is present, then automatically pipetting to dilute the sample and repeating step (g) for the diluted sample.

2. The method according to claim 1, wherein a further wavelength is optionally used for correction/blanking purposes.

3. The method according to claim 1, wherein additional signal(s) measured at the wavelength used for determination of the analyte and/or the wavelength used for the calculation of R and/or at another wavelength, are assessed by comparison with predetermined limit values before calculating and judging the presence of a prozone effect based on the reaction rate ratio R.

4. The method according to claim 1, wherein a predetermined limit value for a signal change in a certain time period is defined, for neglecting samples with extremely low reaction rates from a prozone check and classifying such samples directly as non-prozone samples.

5. The method according to claim 1, wherein a predetermined limit value is defined for a signal change in a certain time period, for deciding if a sample with extremely high reaction rate is immediately categorized as a prozone sample.

6. The method according to claim 1, wherein a predetermined limit value is defined for a signal change in a certain time period, for deciding if a sample with extremely high reaction rate is categorized as a prozone sample, after the calculation of the reaction rate ratio R.

7. The method according to claim 1, wherein specific measurement conditions comprising reaction times, calibration points, calibration mode and the assay type are additionally applied to the measurement protocol.

8. The method according to claim 1, comprising using an instrument platform of a commercially available spectrophotometric laboratory test without applying pre-analytical sample dilution treatment and/or changing the assay procedure by analyte re-addition.

9. A computer-implemented method, performed by a data management system of a photometer instrument platform including a processor and a memory, for determining an amount of albumin in a sample, which may show a prozone effect by photometric assays, wherein the albumin is quantified from a change in an optical signal of a reaction mixture after interaction of the albumin with albumin specific assay reagents, wherein the data management system is in communication with the photometer instrument platform which further includes at least one pipette and at least one reaction cell, wherein the data management system controls the operation of the pipette the method comprising the following steps:
   a) automatically pipetting the reaction mixture comprising the sample and the assay reagent into at least one reaction cell to obtain measurement results;
   b) generating a calibration curve using the data management system for at least one wavelength and reaction time for albumin in a sample to be determined;
   c) depositing the measurement results as an input to the data management system;
   d) measuring simultaneously an optical signal from a first wavelength and at least one second wavelength in a sample over a complete reaction time using a photometer system, wherein the first wavelength is used for the determination of the albumin in the sample, and the second wavelength is used for the determination of the prozone effect in the sample;

e) calculating a reaction rate ratio R using the data management system by using the signal obtained at the at least one second wavelength R=[reaction rate time period 2/reaction rate at time period 1]×100 with reaction rate at time period 2=[signal(time point 4)−signal (time point 3)]/[time point 4−time point3] and reaction rate at time period 1=[signal(time point2)−signal(time point1)]/[time point2−time point1];

f) using the data management system to determine whether a prozone effect is present in the sample by comparison of the R value calculated in step (e) with predetermined limit values;

g) using the data management system to quantify an amount of albumin by comparison of the optical signal obtained at the first wavelength using the photometer system with the calibration curve; wherein h) if step (f) determines that a prozone effect is not present, then the method further comprises reporting the amount quantified in step (g) as the amount of albumin in the sample, and if step (f) determines that a prozone effect is present, then the method further comprises automatically pipetting to dilute the sample and repeating step (g) for the diluted sample.

10. The method according to claim 9, wherein the difference between the first wavelength and the second wavelength is higher than 10 nm.

* * * * *